United States Patent [19]
Smit et al.

[11] Patent Number: 5,500,353
[45] Date of Patent: Mar. 19, 1996

[54] BACTERIAL SURFACE PROTEIN EXPRESSION

[75] Inventors: John Smit, Richmond; Wade H. Bingle, Vancouver, both of Canada

[73] Assignee: The University of British Columbia, Vancouver, Canada

[21] Appl. No.: 194,290

[22] Filed: Feb. 9, 1994

Related U.S. Application Data

[63] Continuation-in-part of Ser. No. 895,367, Jun. 9, 1992, abandoned.

[51] Int. Cl.$^6$ .............................. C12P 21/06; C07K 1/00; A61K 38/00; C07H 19/00
[52] U.S. Cl. ...................... 435/69.1; 435/69.3; 435/69.7; 435/177; 435/209; 435/252.3; 514/6; 530/350; 530/395; 530/400; 536/22.1; 536/23.1; 536/23.4; 536/23.7; 424/197.11; 424/192.1
[58] Field of Search .................................. 435/69.1, 69.3, 435/69.7, 177, 194.67, 209, 252.3; 514/6; 530/350, 395, 400; 536/22.1, 23.1, 23.4, 23.7

[56] References Cited

FOREIGN PATENT DOCUMENTS 2090549  12/1993  Canada .

OTHER PUBLICATIONS

Smit, John; and, Nina Agabian; "Cloning of the Major Protein of the Caulobacter crescentus Periodic Surface Layer: Detection and Characterization of the Cloned Peptide by Protein Expression Assays" (1984) J. Bacteriol. 160, 1137–1145.
Fisher, James A.; John Smit; and, Nina Agabian; "Transcriptional Analysis of the Major Surface Array Gene of Caulobacter crescentus" (1988) J. Bacteriol 170, 4706–4713.
Charbit, Alain; et al; "Versatility of a Vector for Expressing Foreign Polypeptides at the Surface of Gram–Negative Bacteria" (1988) Gene 70, 181–189.
Bingle, Wade H.; and, John Smit; "High–Level Expression Vectors for Caulobacter crescentus Incorporating the Transcription/Translation Initiation Regions of the Paracrystalline Surface–Layer–Protein Gene" (1990) Plasmid 24, 143–148.
Hayes, L. J.; et al; "Chlamydia trachomatis Major Outer Membrane Protein Epitopes Expressed as Fusions with LamB in an Attenuated aroA Strain of Salmonella typhimurium; Their Application as Potential Immunogens" (1991) J. General Microbiology 137, 1557–1564.
Smit, John; and, James Atwater; "Use of Caulobacters to Separate Toxic Heavy Metals from Wastewater Streams" (Apr., 1991) U.S. Department of Energy publication.
Gilchrist, Angus; J. A. Fisher; and, J. Smit; "Nucleotide Sequence Analysis of the Gene Encoding the Caulobacter crescentus Paracrystalline Surface Layer Protein" (Mar., 1992) CAN. J. Microbiol 38, 193–202.
John Smit, "Protein Surface Lakers of Bacteria", in Bacterial Outer Membranes as Model Systems (1986), John Wiley & Sons, Inc. (M. Inouye, ed.); at pp. 344–376.
Koener, J. F., et al, "Nucleotide Sequence of a cDNA Clone Carrying the Glycoprotein Gene of Infectious Hematopoietic Necrosis Virus, a Fish Rhabdovirus" (1987) 61 J. Virology, pp. 1342–1349, at p. 1345.
Gilchrist, A. and Smit, J., "Transformation of Freshwater and Marine Caulobacters by Electroporation" (1991), 173 J. Bacteriology, pp. 921–925.
Smit, J. and Atwater, J., "Use of Caulobacters to Separate Toxic Heavy Metals From Wastewater Streams", in: *Proceedings of Waste Stream Management & Utilization Innovative Concept—An Experimental Technique Exchange* (vol. 1) *Mining & Metals Remediation, Wash. D.C. Apr. 25–26, 1991*, U.S. Department of Energy, Pacific Northwest Lab, Richland, Washington; at pp. 6.1–6.11.
"Federal Grant is First for Manmade Cleanup Bug", in: *Environment Today*, vol. 2, Nov./Dec. 1991.
P. Edwards and J. Smit, "A Transducing Bacteriophage for Caulobacter crescentus Uses the Paracrystalline Surface Layer Protein as a Receptor" (1991) 173 J. Bacteriology, pp. 5568–5572.
W. H. Bingle and J. Smit, "A Method of Tagging Specific–Purpose Linkers with an Antibiotic–Resistance Gene for Linker Mutagenesis Using a Selectable Marker", (1991) 151 BioTechniques, pp. 150–152.
Walker, S. G. et al, "Isolation and Comparison of the Paracrystalline Surface Layer Proteins of Freshwater Caulobacters", (1992) 174 J. Bacteriology, pp. 1783–1792.
Bingle, W. H., et al, "Caulobacters as Potential Biological Agents for Treatment of Pulp and Paper Effluent: Sequentration of Heavy Metals and Depolymerization of Cellulose", in: *BioforBioqual '92*, Vancouver, Canada, Jun. 9–11, 1992.
Bingle, W. H., et al, "Definition of Form and Function for the S–Layer of Caulobacter crescentus" in: *Advances in Bacterial Paracrystalline Surface Layers* (1993) Plenum Press (T. J. Beveridge and S. F. Koval ed.), pp. 181–197 (see enclosed author's copy insert at pp. 9–11).
Bingle, W. H., et al, "Linker Mutagenesis of the Caulobacter crescentus S–Layer Protein", in: *Advances in Bacterial Paracrystalline Surface Layers* (1993) Plenum Press (T. J. Beveridge and S. F. Koval ed.), pp. 293–296.
T. J. Beveridge, et al, "Summary Statements", in: *Advances in Bacterial Paracrystalline Surfaces Layers* (1993) Plenum Press (T. J. Beveridge and S. F. Koval, ed.), pp. 323–327; at p. 325.

*Primary Examiner*—Robert A. Wax
*Assistant Examiner*—Hyosuk Kim
*Attorney, Agent, or Firm*—Shlesinger, Arkwright & Garvey

[57] ABSTRACT

This invention provides a bacterium having an S-layer modified such that the bacterium S-layer protein gene contains one or more in-frame sequences coding for one or more heterologous polypeptides and, the S-layer is a fusion product of the S-layer protein and the heterologous polypeptide. The bacterium is preferably a Caulobacter which may be cultured as a film in a bioreactor or may be used to present an antigenic epitope to the environment of the bacterium. This invention also provides a method of expressing and presenting to the environment of a Caulobacter, a polypeptide that is heterologous to the S-layer of Caulobacter which comprises cloning a coding sequence for the polypeptide in-frame into an S-layer protein gene of Caulobacter whereby the polypeptide is expressed and presented on the surface of the Caulobacter as a fusion product of the S-layer protein and the polypeptide in the S-layer of the Caulobacter.

5 Claims, 9 Drawing Sheets

```
 735        A  V  N  V  G  L  T  V  L  A  A  P  T  G  T  T  V  T  L  A  N  A  T  G  T  S  D  V  F  N  L  T
2200        TTGCGGGTGAATGTCGGGCCTGACCGTTCTGGCGGCACCGACCGGTACGACGGTGACCCTGGCCAACGCCACGGGCACCTCGGACGTGTTCAACCTGAC

768        L  S  S  S  A  A  L  A  A  G  T  V  A  L  A  G  V  E  T  V  N  I  A  A  T  D  T  N  T  T  A  H  V
2300        CCTGTCGTCCTCGGCCGCTCTGGCCGCCGGTACGGTTGCGCTGGCCGGTGTCGAGACGGTGAACATCGCCGCCACCGACACCAACACGACCGCTCACGTC

801        D  T  L  T  L  Q  A  T  S  A  K  S  I  V  V  T  G  N  A  G  L  N  L  T  N  T  G  N  T  A  V  T  S  F
2400        GACACGCTGACGCTGCAAGCCACCTCGGCCAAGTCGATCGTGGTGACGGGCAACGCCGGTCTGAACCTGACCAACACCGGCAACACGGCTGTCACCAGCT

835        D  A  S  A  V  T  G  T  G  S  A  V  T  F  V  S  A  N  T  T  V  G  E  V  V  T  R  G  G  A  G  A
2500        TCGACGCCAGCGCCGTCACCGGCACGGGCTCCGGCGCCGTGACCTTCGTGTCGGCCAACACCACCGTGGGTGAAGTCGTCACGATCCGGGGCGGCGC

868        D  S  L  I  G  S  A  T  A  N  D  T  I  I  G  G  A  G  A  D  T  L  V  Y  T  G  G  T  D  T  E  I  G
2600        CGACTCGCTGATCGGTTCGGCCACCGCCAACGACACCATCATCGGTGGGGCTGGCGCCGACACCCTGGTCTACACCGGCGGGACACTTCACGGGT

901        G  I  G  A  D  I  F  D  I  N  A  I  G  T  S  T  A  F  V  T  I  T  D  A  A  V  G  D  K  L  D  L  V  G
2700        GGCACGGGCGCGGATATCTTCGATATCAACGCTATCGGCACCTCGACCGCCTTCGTGACGATCACCGACGCCGCCGTCGGCGACAAGCTCGACCTCGTCG

935        I  S  T  N  G  A  I  A  D  G  A  F  G  A  A  V  T  L  G  A  A  A  T  L  A  Q  Y  L  D  A  A  A  A
2800        GCATCTCGACGAACGGCGCTATCGCTGACGGCGCCTTCGGCGCCGTGACCCTGGGCGCTGCGGCAACGCTCGCCCAGTACCTCGACGCCGCTGCTGCC

968        G  D  G  S  G  T  S  V  A  K  W  F  Q  F  G  G  D  T  Y  V  V  V  D  S  S  A  G  A  T  F  V  S  G
2900        CGGGCGACGGCAGCGGCACGTCGGTTGCCAAGTGGTTCCAGTTCGGCGGCGACACCTATGTCGTCGTTGACAGCTCGGCCGACCTTCGTCAGCGGC

1001        A  D  A  V  I  K  L  T  G  L  V  T  L  T  T  S  A  F  A  T  E  V  L  T  L  A end
3000        GCTGACGCGGTGATCAAGCTGACCGGTCTGGTCACGCTGACCACCTCGGCCTTCGCCACCGAAGTCCTGACGCTCGCCTAAGGCGAACGTCTGATCCTCGC 3100        CTAGGCGAGGATCGCTAGACTAAGAGACCCGTCTTCCGAAAGGAGGCGGGTCTTTCTTATGGGCCGCTACGCGCTGGCCGGCCTTGCCTAGTTCCGGT
```

FIG. 6c

```
  1                                                          10
arg   ser   pro   his   pro   gly   ile   asn   asp   val
CGA   TCT   CCA   CAT   CCC   GGA   ATA   AAT   GAC   GTC 20
tyr   ala   met   his   lys   gly   ser   ile   tyr   his
TAC   GCT   ATG   CAC   AAA   GGC   TCC   ATC   TAT   CAC 30
gly   met   cys   met   thr   val   ala   val   asp   glu
GGG   ATG   TCC   ATG   ACG   GTC   GCT   GTG   GAC   GAG 40
val   ser   lys   asp   arg   thr   thr   tyr   arg   ala
GTA   TCC   AAG   GAC   AGG   ACG   ACG   TAC   AGG   GCC 50
his   arg   ala   thr   ser   phe   thr   lys   trp   glu
CAT   CGC   GCT   ACC   AGC   TTC   ACG   AAA   TGG   GAA 60
arg   pro   phe   gly   asp   glu   trp   glu   gly   phe
CGA   CCC   TTT   GGG   GAT   GAG   TGG   GAG   GGC   TTT 70
his   gly   leu   his   gly   asn   asn   thr   thr   ile
CAC   GGA   TTG   CAC   GGA   AAC   AAC   ACC   ACC   ATT 80
ile   pro   asp   leu   glu   lys   tyr   val   ala   gln
ATT   CCA   GAC   CTG   GAG   AAA   TAC   GTC   GCC   CAG 90
tyr   lys   thr   ser   met   met   glu   pro   met   ser
TAC   AAG   ACG   AGC   ATG   ATG   GAA   CCG   ATG   AGC 100
ile   lys   ser   val   pro   his   pro   ser   ile   leu
ATC   AAA   TCC   GTA   CCC   CAT   CCA   AGC   ATC   CTG 110
ala   phe   tyr   asn   glu   thr   asp   leu   ser   gly
GCC   TTC   TAC   AAT   GAG   ACA   GAC   TTA   TCA   GGG
```

FIG. 9

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
ACGTCCTAGG  CGAGCTCCAG  CTGGCTCCGG  AGGTCTAGAC  CTAG                44
```

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
GTCGACGGGA  TCC                                                     13
```

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GGATCCGCGT CGAC                                                                                    14
```

( 2 ) INFORMATION FOR SEQ ID NO:4:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:4:

```
GTCGACGCGG ATCC                                                                                    14
```

( 2 ) INFORMATION FOR SEQ ID NO:5:

( i ) SEQUENCE CHARACTERISTICS:
    ( A ) LENGTH: 13 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:5:

```
GGATCCCGTC GAC                                                                                     13
```

( 2 ) INFORMATION FOR SEQ ID NO:6:

( i ) SEQUENCE CHARACTERISTICS:
    ( A ) LENGTH: 3300 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Caulobacter crescentus
    ( B ) STRAIN: CB 15

( x i ) SEQUENCE DESCRIPTION: SEQ ID NO:6:

```
GCTATTGTCG ACGTATGACG TTTGCTCTAT AGCCATCGCT GCTCCCATGC GCGCCACTCG          60
GTCGCAGGGG GTGTGGGATT TTTTTTGGGA GACAATCCTC ATGGCCTATA CGACGGCCCA         120
GTTGGTGACT GCGTACACCA ACGCCAACCT CGGCAAGGCG CCTGACGCCG CCACCACGCT         180
GACGCTCGAC GCGTACGCGA CTCAAACCCA GACGGGCGGC CTCTCGGACG CCGCTGCGCT         240
GACCAACACC CTGAAGCTGG TCAACAGCAC GACGGCTGTT GCCATCCAGA CCTACCAGTT         300
CTTCACCGGC GTTGCCCCGT CGGCCGCTGG TCTGGACTTC CTGGTCGACT CGACCACCAA         360
CACCAACGAC CTGAACGACG CGTACTACTC GAAGTTCGCT CAGGAAAACC GCTTCATCAA         420
CTTCTCGATC AACCTGGCCA CGGGCGCCGG CGCCGGCGCG ACGGCTTTCG CCGCCGCCTA         480
CACGGGCGTT TCGTACGCCC AGACGGTCGC CACCGCCTAT GACAAGATCA TCGGCAACGC         540
CGTCGCGACC GCCGCTGGCG TCGACGTCGC GGCCGCCGTG GCTTTCCTGA GCCGCCAGGC         600
CAACATCGAC TACCTGACCG CCTTCGTGCG CGCCAACACG CCGTTCACGG CCGCTGCCGA         660
CATCGATCTG GCCGTCAAGG CCGCCCTGAT CGGCACCATC CTGAACGCCG CCACGGTGTC         720
GGGCATCGGT GGTTACGCGA CCGCCACGGC CGCGATGATC AACGACCTGT CGGACGGCGC         780
CCTGTCGACC GACAACGCGG CTGGCGTGAA CCTGTTCACC GCCTATCCGT CGTCGGGCGT         840
GTCGGGTTCG ACCCTCTCGC TGACCACCGG CACCGACACC CTGACGGGCA CCGCCAACAA         900
CGACACGTTC GTTGCGGGTG AAGTCGCCGG CGCTGCGACC CTGACCGTTG GCGACACCCT         960
GAGCGGCGGT GCTGGCACCG ACGTCCTGAA CTGGGTGCAA GCTGCTGCGG TTACGGCTCT        1020
```

-continued

| | | | | | | |
|---|---|---|---|---|---|---|
| GCCGACCGGC | GTGACGATCT | CGGGCATCGA | AACGATGAAC | GTGACGTCGG | GCGCTGCGAT | 1080 |
| CACCCTGAAC | ACGTCTTCGG | GCGTGACGGG | TCTGACCGCC | CTGAACACCA | ACACCAGCGG | 1140 |
| CGCGGCTCAA | ACCGTCACCG | CCGGCGCTGG | CCAGAACCTG | ACCGCCACGA | CCGCCGCTCA | 1200 |
| AGCCGCGAAC | AACGTCGCCG | TCGACGGGCG | CGCCAACGTC | ACCGTCGCCT | CGACGGGCGT | 1260 |
| GACCTCGGGC | ACGACCACGG | TCGGCGCCAA | CTCGGCCGCT | TCGGGCACCG | TGTCGGTGAG | 1320 |
| CGTCGCGAAC | TCGAGCACGA | CCACCACGGG | CGCTATCGCC | GTGACCGGTG | GTACGGCCGT | 1380 |
| GACCGTGGCT | CAAACGGCCG | GCAACGCCGT | GAACACCACG | TTGACGCAAG | CCGACGTGAC | 1440 |
| CGTGACCGGT | AACTCCAGCA | CCACGGCCGT | GACGGTCACC | CAAACCGCCG | CCGCCACCGC | 1500 |
| CGGCGCTACG | GTCGCCGGTC | GCGTCAACGG | CGCTGTGACG | ATCACCGACT | CTGCCGCCGC | 1560 |
| CTCGGCCACG | ACCGCCGGCA | AGATCGCCAC | GGTCACCCTG | GGCAGCTTCG | GCGCCGCCAC | 1620 |
| GATCGACTCG | AGCGCTCTGA | CGACCGTCAA | CCTGTCGGGC | ACGGGCACCT | CGCTCGGCAT | 1680 |
| CGGCCGCGGC | GCTCTGACCG | CCACGCCGAC | CGCCAACACC | CTGACCCTGA | ACGTCAATGG | 1740 |
| TCTGACGACG | ACCGGCGCGA | TCACGGACTC | GGAAGCGGCT | GCTGACGATG | GTTTCACCAC | 1800 |
| CATCAACATC | GCTGGTTCGA | CCGCCTCTTC | GACGATCGCC | AGCCTGGTGG | CCGCCGACGC | 1860 |
| GACGACCCTG | AACATCTCGG | GCGACGCTCG | CGTCACGATC | ACCTCGCACA | CCGCTGCCGC | 1920 |
| CCTGACGGGC | ATCACGGTGA | CCAACAGCGT | TGGTGCGACC | CTCGGCGCCG | AACTGGCGAC | 1980 |
| CGGTCTGGTC | TTCACGGGCG | GCGCTGGCCG | TGACTCGATC | CTGCTGGGCG | CCACGACCAA | 2040 |
| GGCGATCGTC | ATGGGCGCCG | GCGACGACAC | CGTCACCGTC | AGCTCGGCGA | CCCTGGGCGC | 2100 |
| TGGTGGTTCG | GTCAACGGCG | GCGACGGCAC | CGACGTTCTG | GTGGCCAACG | TCAACGGTTC | 2160 |
| GTCGTTCAGC | GCTGACCCGG | CCTTCGGCGG | CTTCGAAACC | CTCCGCGTCG | CTGGCGCGGC | 2220 |
| GGCTCAAGGC | TCGCACAACG | CCAACGGCTT | CACGGCTCTG | CAACTGGGCG | CGACGGCGGG | 2280 |
| TGCGACGACC | TTCACCAACG | TTGCGGTGAA | TGTCGGCCTG | ACCGTTCTGG | CGGCTCCGAC | 2340 |
| CGGTACGACG | ACCGTGACCC | TGGCCAACGC | CACGGGCACC | TCGGACGTGT | CAACCTGAC | 2400 |
| CCTGTCGTCC | TCGGCCGCTC | TGGCCGCTGG | TACGGTTGCG | CTGGCTGGCG | TCGAGACGGT | 2460 |
| GAACATCGCC | GCCACCGACA | CCAACACGAC | CGCTCACGTC | GACACGCTGA | CGCTGCAAGC | 2520 |
| CACCTCGGCC | AAGTCGATCG | TGGTGACGGG | CAACGCCGGT | CTGAACCTGA | CCAACACCGG | 2580 |
| CAACACGGCT | GTCACCAGCT | TCGACGCCAG | CGCCGTCACC | GGCACGGCTC | CGGCTGTGAC | 2640 |
| CTTCGTGTCG | GCCAACACCA | CGGTGGGTGA | AGTCGTCACG | ATCCGCGGCG | CGCTGGCGC | 2700 |
| CGACTCGCTG | ACCGGTTCGG | CCACCGCCAA | TGACACCATC | ATCGGTGGCG | CTGGCGCTGA | 2760 |
| CACCCTGGTC | TACACCGGCG | GTACGGACAC | CTTCACGGGT | GGCACGGGCG | CGGATATCTT | 2820 |
| CGATATCAAC | GCTATCGGCA | CCTCGACCGC | TTTCGTGACG | ATCACCGACG | CCGCTGTCGG | 2880 |
| CGACAAGCTC | GACCTCGTCG | GCATCTCGAC | GAACGGCGCT | ATCGCTGACG | GCGCCTTCGG | 2940 |
| CGCTGCGGTC | ACCCTGGGCG | CTGCTGCGAC | CCTGGCTCAG | TACCTGGACG | CTGCTGCTGC | 3000 |
| CGGCGACGGC | AGCGGCACCT | CGGTTGCCAA | GTGGTTCCAG | TTCGGCGGCG | ACACCTATGT | 3060 |
| CGTCGTTGAC | AGCTCGGCTG | GCGCGACCTT | CGTCAGCGGC | GCTGACGCGG | TGATCAAGCT | 3120 |
| GACCGGTCTG | GTCACGCTGA | CCACCTCGGC | CTTCGCCACC | GAAGTCCTGA | CGCTCGCCTA | 3180 |
| AGCGAACGTC | TGATCCTCGC | CTAGGCGAGG | ATCGCTAGAC | TAAGAGACCC | CGTCTTCCGA | 3240 |
| AAGGGAGGCG | GGGTCTTTCT | TATGGGCGCT | ACGCGCTGGC | CGGCCTTGCC | TAGTTCCGGT | 3300 |

( 2 ) INFORMATION FOR SEQ ID NO:7:

( i ) SEQUENCE CHARACTERISTICS:

( A ) LENGTH: 1026 amino acids
( B ) TYPE: amino acid
( D ) TOPOLOGY: linear ( i i ) MOLECULE TYPE: protein ( x i ) SEQUENCE DESCRIPTION: SEQ ID NO:7:

| Met<br>1 | Ala | Tyr | Thr | Thr<br>5 | Ala | Gln | Leu | Val | Thr<br>10 | Ala | Tyr | Thr | Asn | Ala<br>15 | Asn |
|---|---|---|---|---|---|---|---|---|---|---|---|---|---|---|---|
| Leu | Gly | Lys | Ala<br>20 | Pro | Asp | Ala | Ala | Thr<br>25 | Thr | Leu | Thr | Leu | Asp<br>30 | Ala | Tyr |
| Ala | Thr | Gln<br>35 | Thr | Gln | Thr | Gly<br>40 | Gly | Leu | Ser | Asp | Ala<br>45 | Ala | Ala | Leu | Thr |
| Asn | Thr<br>50 | Leu | Lys | Leu | Val<br>55 | Asn | Ser | Thr | Thr | Ala<br>60 | Val | Ala | Ile | Gln | Thr |
| Tyr<br>65 | Gln | Phe | Phe | Thr | Gly<br>70 | Val | Ala | Pro | Ser | Ala<br>75 | Ala | Gly | Leu | Asp | Phe<br>80 |
| Leu | Val | Asp | Ser | Thr<br>85 | Thr | Asn | Thr | Asn | Asp<br>90 | Leu | Asn | Asp | Ala | Tyr<br>95 | Tyr |
| Ser | Lys | Phe | Ala<br>100 | Gln | Glu | Asn | Arg | Phe<br>105 | Ile | Asn | Phe | Ser | Ile<br>110 | Asn | Leu |
| Ala | Thr | Gly<br>115 | Ala | Gly | Ala | Gly | Ala<br>120 | Thr | Ala | Phe | Ala | Ala<br>125 | Ala | Tyr | Thr |
| Gly | Val<br>130 | Ser | Tyr | Ala | Gln | Thr<br>135 | Val | Ala | Thr | Ala | Tyr<br>140 | Asp | Lys | Ile | Ile |
| Gly<br>145 | Asn | Ala | Val | Ala | Thr<br>150 | Ala | Ala | Gly | Val | Asp<br>155 | Val | Ala | Ala | Ala | Val<br>160 |
| Ala | Phe | Leu | Ser | Arg<br>165 | Gln | Ala | Asn | Ile | Asp<br>170 | Tyr | Leu | Thr | Ala | Phe<br>175 | Val |
| Arg | Ala | Asn | Thr<br>180 | Pro | Phe | Thr | Ala | Ala<br>185 | Ala | Asp | Ile | Asp | Leu<br>190 | Ala | Val |
| Lys | Ala | Ala<br>195 | Leu | Ile | Gly | Thr | Ile<br>200 | Leu | Asn | Ala | Ala | Thr<br>205 | Val | Ser | Gly |
| Ile | Gly<br>210 | Gly | Tyr | Ala | Thr | Ala<br>215 | Thr | Ala | Ala | Met | Ile<br>220 | Asn | Asp | Leu | Ser |
| Asp<br>225 | Gly | Ala | Leu | Ser | Thr<br>230 | Asp | Asn | Ala | Ala | Gly<br>235 | Val | Asn | Leu | Phe | Thr<br>240 |
| Ala | Tyr | Pro | Ser | Ser<br>245 | Gly | Val | Ser | Gly | Ser<br>250 | Thr | Leu | Ser | Leu | Thr<br>255 | Thr |
| Gly | Thr | Asp | Thr<br>260 | Leu | Thr | Gly | Thr | Ala<br>265 | Asn | Asn | Asp | Thr | Phe<br>270 | Val | Ala |
| Gly | Glu | Val<br>275 | Ala | Gly | Ala | Ala | Thr<br>280 | Leu | Thr | Val | Gly | Asp<br>285 | Thr | Leu | Ser |
| Gly | Gly<br>290 | Ala | Gly | Thr | Asp | Val<br>295 | Leu | Asn | Trp | Val | Gln<br>300 | Ala | Ala | Ala | Val |
| Thr<br>305 | Ala | Leu | Pro | Thr | Gly<br>310 | Val | Thr | Ile | Ser | Gly<br>315 | Ile | Glu | Thr | Met | Asn<br>320 |
| Val | Thr | Ser | Gly | Ala<br>325 | Ala | Ile | Thr | Leu | Asn<br>330 | Thr | Ser | Ser | Gly | Val<br>335 | Thr |
| Gly | Leu | Thr | Ala<br>340 | Leu | Asn | Thr | Asn | Thr<br>345 | Ser | Gly | Ala | Ala | Gln<br>350 | Thr | Val |
| Thr | Ala | Gly<br>355 | Ala | Gly | Gln | Asn | Leu<br>360 | Thr | Ala | Thr | Ala<br>365 | Ala | Gln | Ala |
| Ala | Asn | Asn | Val | Ala | Val | Asp<br>375 | Gly | Gly | Ala | Asn | Val<br>380 | Thr | Val | Ala | Ser |

```
Thr  Gly  Val  Thr  Ser  Gly  Thr  Thr  Val  Gly  Ala  Asn  Ser  Ala  Ala
385                 390                 395                           400

Ser  Gly  Thr  Val  Ser  Val  Ser  Val  Ala  Asn  Ser  Ser  Thr  Thr  Thr
                    405                 410                 415

Gly  Ala  Ile  Ala  Val  Thr  Gly  Gly  Thr  Ala  Val  Thr  Val  Ala  Gln  Thr
               420            425                           430

Ala  Gly  Asn  Ala  Val  Asn  Thr  Thr  Leu  Thr  Gln  Ala  Asp  Val  Thr  Val
          435                 440                      445

Thr  Gly  Asn  Ser  Ser  Thr  Thr  Ala  Val  Thr  Val  Thr  Gln  Thr  Ala  Ala
     450                      455                 460

Ala  Thr  Ala  Gly  Ala  Thr  Val  Ala  Gly  Arg  Val  Asn  Gly  Ala  Val  Thr
465                      470                 475                           480

Ile  Thr  Asp  Ser  Ala  Ala  Ser  Ala  Thr  Thr  Ala  Gly  Lys  Ile  Ala
               485                      490                      495

Thr  Val  Thr  Leu  Gly  Ser  Phe  Gly  Ala  Ala  Thr  Ile  Asp  Ser  Ser  Ala
               500                 505                      510

Leu  Thr  Thr  Val  Asn  Leu  Ser  Gly  Thr  Gly  Thr  Ser  Leu  Gly  Ile  Gly
          515                      520                 525

Arg  Gly  Ala  Leu  Thr  Ala  Thr  Pro  Thr  Ala  Asn  Thr  Leu  Thr  Leu  Asn
     530                 535                      540

Val  Asn  Gly  Leu  Thr  Thr  Thr  Gly  Ala  Ile  Thr  Asp  Ser  Glu  Ala  Ala
545                 550                 555                           560

Ala  Asp  Asp  Gly  Phe  Thr  Thr  Ile  Asn  Ile  Ala  Gly  Ser  Thr  Ala  Ser
               565                 570                      575

Ser  Thr  Ile  Ala  Ser  Leu  Val  Ala  Ala  Asp  Ala  Thr  Thr  Leu  Asn  Ile
               580                 585                      590

Ser  Gly  Asp  Ala  Arg  Val  Thr  Ile  Thr  Ser  His  Thr  Ala  Ala  Ala  Leu
          595                 600                      605

Thr  Gly  Ile  Thr  Val  Thr  Asn  Ser  Val  Gly  Ala  Thr  Leu  Gly  Ala  Glu
     610                 615                      620

Leu  Ala  Thr  Gly  Leu  Val  Phe  Thr  Gly  Gly  Ala  Gly  Ala  Asp  Ser  Ile
625                 630                 635                           640

Leu  Leu  Gly  Ala  Thr  Thr  Lys  Ala  Ile  Val  Met  Gly  Ala  Gly  Asp  Asp
               645                      650                           655

Thr  Val  Thr  Val  Ser  Ser  Ala  Thr  Leu  Gly  Ala  Gly  Gly  Ser  Val  Asn
               660                      665                 670

Gly  Gly  Asp  Gly  Thr  Asp  Val  Leu  Val  Ala  Asn  Val  Asn  Gly  Ser  Ser
          675                      680                 685

Phe  Ser  Ala  Asp  Pro  Ala  Phe  Gly  Gly  Phe  Glu  Thr  Leu  Arg  Val  Ala
     690                      695                 700

Gly  Ala  Ala  Ala  Gln  Gly  Ser  His  Asn  Ala  Asn  Gly  Phe  Thr  Ala  Leu
705                 710                      715                           720

Gln  Leu  Gly  Ala  Thr  Ala  Gly  Ala  Thr  Thr  Phe  Thr  Asn  Val  Ala  Val
               725                 730                           735

Asn  Val  Gly  Leu  Thr  Val  Leu  Ala  Ala  Pro  Thr  Gly  Thr  Thr  Thr  Val
               740                 745                 750

Thr  Leu  Ala  Asn  Ala  Thr  Gly  Thr  Ser  Asp  Val  Phe  Asn  Leu  Thr  Leu
          755                 760                      765

Ser  Ser  Ser  Ala  Ala  Leu  Ala  Ala  Gly  Thr  Val  Ala  Leu  Ala  Gly  Val
     770                 775                      780

Glu  Thr  Val  Asn  Ile  Ala  Ala  Thr  Asp  Thr  Asn  Thr  Thr  Ala  His  Val
785                      790                      795                      800

Asp  Thr  Leu  Thr  Leu  Gln  Ala  Thr  Ser  Ala  Lys  Ser  Ile  Val  Val  Thr
               805                      810                      815
```

```
Gly  Asn  Ala  Gly  Leu  Asn  Leu  Thr  Asn  Thr  Gly  Asn  Thr  Ala  Val  Thr
               820                      825                      830

Ser  Phe  Asp  Ala  Ser  Ala  Val  Thr  Gly  Thr  Gly  Ser  Ala  Val  Thr  Phe
          835                      840                      845

Val  Ser  Ala  Asn  Thr  Thr  Val  Gly  Glu  Val  Val  Thr  Ile  Arg  Gly  Gly
     850                      855                      860

Ala  Gly  Ala  Asp  Ser  Leu  Thr  Gly  Ser  Ala  Thr  Ala  Asn  Asp  Thr  Ile
865                      870                      875                      880

Ile  Gly  Gly  Ala  Gly  Ala  Asp  Thr  Leu  Val  Tyr  Thr  Gly  Gly  Thr  Asp
               885                      890                      895

Thr  Phe  Thr  Gly  Gly  Thr  Gly  Ala  Asp  Ile  Phe  Asp  Ile  Asn  Ala  Ile
               900                      905                      910

Gly  Thr  Ser  Thr  Ala  Phe  Val  Thr  Ile  Thr  Asp  Ala  Ala  Val  Gly  Asp
          915                      920                      925

Lys  Leu  Asp  Leu  Val  Gly  Ile  Ser  Thr  Asn  Gly  Ala  Ile  Ala  Asp  Gly
     930                      935                      940

Ala  Phe  Gly  Ala  Ala  Val  Thr  Leu  Gly  Ala  Ala  Ala  Thr  Leu  Ala  Gln
945                      950                      955                      960

Tyr  Leu  Asp  Ala  Ala  Ala  Ala  Gly  Asp  Gly  Ser  Gly  Thr  Ser  Val  Ala
               965                      970                      975

Lys  Trp  Phe  Gln  Phe  Gly  Gly  Asp  Thr  Tyr  Val  Val  Val  Asp  Ser  Ser
               980                      985                      990

Ala  Gly  Ala  Thr  Phe  Val  Ser  Gly  Ala  Asp  Ala  Val  Ile  Lys  Leu  Thr
          995                      1000                     1005

Gly  Leu  Val  Thr  Leu  Thr  Thr  Ser  Ala  Phe  Ala  Thr  Glu  Val  Leu  Thr
     1010                     1015                     1020

Leu  Ala
1025
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Xaa  Cys  Thr  Ser  Asp  Gln  Asp  Glu  Gln  Phe  Ile  Pro  Lys  Gly  Cys  Ser
1                   5                        10                      15

Xaa
```

( 2 ) INFORMATION FOR SEQ ID NO:9:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Arg  Ser  Pro  His  Pro  Gly  Ile  Asn  Asp  Val  Tyr  Ala  Met  His  Lys  Gly
1                   5                        10                      15

Ser  Ile  Tyr  His  Gly  Met  Cys  Met  Thr  Val  Ala  Val  Asp  Glu  Val  Ser
               20                      25                      30

Lys  Asp  Arg  Thr  Thr  Tyr  Arg  Ala  His  Arg  Ala  Thr  Ser  Phe  Thr  Lys
          35                      40                      45
```

| | | | | | | | | | | | | | | |
|---|---|---|---|---|---|---|---|---|---|---|---|---|---|---|
| Trp | Glu | Arg | Pro | Phe | Gly | Asp | Glu | Trp | Glu | Gly | Phe | His | Gly | Leu | His |
| | 50 | | | | | 55 | | | | | 60 | | | | |
| Gly | Asn | Asn | Thr | Thr | Ile | Ile | Pro | Asp | Leu | Glu | Lys | Tyr | Val | Ala | Gln |
| 65 | | | | | 70 | | | | | 75 | | | | | 80 |
| Tyr | Lys | Thr | Ser | Met | Met | Glu | Pro | Met | Ser | Ile | Lys | Ser | Val | Pro | His |
| | | | | 85 | | | | | 90 | | | | | 95 | |
| Pro | Ser | Ile | Leu | Ala | Phe | Tyr | Asn | Glu | Thr | Asp | Leu | Ser | Gly | | |
| | | | 100 | | | | | 105 | | | | | 110 | | |

( 2 ) INFORMATION FOR SEQ ID NO:10:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:10:

| | | | | | |
|---|---|---|---|---|---|
| CGATCTCCAC | ATCCCGGAAT | AAATGACGTC | TACGCTATGC | ACAAAGGCTC | CATCTATCAC | 60 |
| GGGATGTCCA | TGACGGTCGC | TGTGGACGAG | GTATCCAAGG | ACAGGACGAC | GTACAGGGCC | 120 |
| CATCGCGCTA | CCAGCTTCAC | GAAATGGGAA | CGACCCTTTG | GGGATGAGTG | GGAGGGCTTT | 180 |
| CACGGATTGC | ACGGAAACAA | CACCACCATT | ATTCCAGACC | TGGAGAAATA | CGTCGCCAG | 240 |
| TACAAGACGA | GCATGATGGA | ACCGATGAGC | ATCAAATCCG | TACCCCATCC | AAGCATCCTG | 300 |
| GCCTTCTACA | ATGAGACAGA | CTTATCAGGG | | | | 330 |

BACTERIAL SURFACE PROTEIN EXPRESSION

This is a continuation-in-part of application Ser. No. 07/895,367, filed Jun. 9, 1992, now abandoned.

FIELD OF THE INVENTION

This invention relates to the expression of heterologous proteins, or portions of such proteins, from genes cloned in a bacteria wherein the expressed protein is fused with a surface protein of the bacterium.

BACKGROUND OF THE INVENTION

Bacterial surface proteins have been used as carriers or vehicles of foreign epitopes expressed in the bacterium (particularly in Salmonella and *E. coli*) for various purposes, including the development of live vaccines. In some instances, the heterologous protein is expressed as a fusion product with a surface protein of the bacterium. Generally, the use of such surface proteins as a vehicle for expression and presentation of heterologous proteins has been limited by the characteristics of the particular surface protein involved. The bacterium's lipopolysaccharide layer, which tends to stimulate a strong immune response, also covers the integral outer membrane proteins of the organism and potentially affects efficient presentation of a cloned epitope. Also, where the surface protein is functional, for example, as part of a filamentous portion of the bacterial cell surface, there will be limited opportunities to express a fusion product and still retain the surface protein's function. Generally, the organisms that have been used for these purposes have been chosen because of the advantages presented in respect of the organism's relationship to its host.

Many genera of bacteria assemble layers composed of repetitive, regularly aligned, proteinaceous sub-units on the outer surface of the cell. These layers are essentially two-dimensional paracrystalline arrays, and being the outer molecular layer of the organism, directly interface with the environment. Such layers are commonly known as S-layers and are found on members of every taxonomic group of walled bacteria including: Archaebacteria; Chlamydia; Cyanobacteria; Acinetobacter; Bacillus; Aquaspirrillum; Caulobacter; Clostridium; Chromatium. (see: Smit, J.; *PROTEIN SURFACE LAYERS OF BACTERIA;* in: "Offprints From Bacterial Outer Membranes As Model Systems" (1986) Dr. M. Inouye (Ed.); John Wylie and Sons, Inc.).

Typically, an S-layer will be composed of an intricate, geometric array of at least one major protein having a repetitive regular structure. In many cases, such as in Caulobacter, the S-layer protein is synthesized by the cell in large quantities and the S-layer completely envelopes the cell and thus appears to be a protective layer.

Caulobacter bacteria are natural inhabitants of most soil and freshwater environments and may persist in waste water treatment systems and effluents. The bacteria alternate between a stalked cell that is attached to a surface and a motile dispersal cell that has adhesive material already expressed and is searching to find a new surface upon which to stick and convert to a stalked cell. The bacteria attach tenaciously to nearly all surfaces and do so without producing the extracelluar enzymes or polysaccharide "slimes" that are characteristic of most other surface attached bacteria. They have simple requirements for growth. The organism is ubiquitous in the environment and has been isolated from oligotrophic to mesotrophic situations. Caulobacters are known for their ability to tolerate low nutrient level stresses, for example, low phosphate levels. This nutrient can be limiting in many leachate waste streams, especially those with high levels of iron or calcium.

The S-layer of *Caulobacter crescentus* has been well characterised. Nearly all freshwater isolates of Caulobacter elaborate an S-layer visibly indistinguishable from the one produced by *Caulobacter crescentus* strains CB2 and CB15. The S-layer proteins from these strains have approximately 100,000 m.w. The protein has been characterized both structurally and chemically. It is composed of ring-like structures spaced at 22 nm intervals arranged in a hexagonal manner on the outer membrane. The S-layer is bound to the bacterial surface by calcium ions and may be removed by low pH treatment or by treatment with a calcium chelator such as EGTA.

The S-layer proteins of S-layer producing strains of Caulobacter have significant similarity. Thus a cloned S-layer protein gene of one Caulobacter strain will likely be useful to retrieve the corresponding genes in other Caulobacter strains (see: Walker, S. G., S. H. Smith, and J. Smit (1992) "Isolation and Comparison of the Paracrystalline Surface Layer Proteins of Freshwater Caulobacters". J. Bacteriol. 174: 1783–1792; and, MacRae, J. O. and, J. Smit (1991) "Characterization of Caulobacters Isolated from Wastewater Treatment Systems" Applied and Environmental Microbiology 57:751–758).

Expression and presentation of a heterologous polypeptide as a fusion product with an S-layer protein of a bacterium would provide advantages not previously seen in systems using organisms such as *E. coli* and Salmonella where fusion products of other kinds of surface proteins have been expressed. Firstly, many bacteria producing S-layer proteins (particulary Caulobacter) are relatively harmless and ubiquitous in the environment. In contrast, many Salmonella and *E. coli* strains are pathogens. Consequently, expression and presentation of a heterologous polypeptide using Caulobacter as a vehicle will have the advantage that the expression system will be stable in a variety of outdoor environments and may not present problems associated with the use of a pathogenic organism. Second, many such bacteria, including Caulobacter, are natural biofilm forming species and may be adapted for use in fixed biofilm bioreactors. Finally, the quantity of the S-layer protein that is synthesized by the bacterium and the unique characteristics of the repetitive, two-dimensional S-layer would make such bacteria ideal for use as an expression system and a "presentation surface" for heterologous polypeptides. Such a presentation surface is desirable in a live vaccine so that presentation of a foreign epitope is maximized. In addition, use of the presentation surface to achieve maximal exposure of a desired polypeptide to the environment results in such bacteria being particularly suited for use in bioreactors or as carriers for the polypeptide in aqueous or terrestrial outdoor environments.

SUMMARY OF INVENTION

This invention provides a method of expressing and presenting to the environment of a Caulobacter, a polypeptide that is heterologous to an S-layer of the Caulobacter, which method comprises cloning a coding sequence for the polypeptide in-frame into an S-layer protein gene of Caulobacter whereby the polypeptide is expressed and presented on the surface of the Caulobacter as a fusion product with the S-layer protein in an S-layer of the Caulobacter.

This invention provides a bacterium having an S-layer wherein a gene of the bacterium encoding an S-layer protein contains one or more in-frame sequences encoding one or more heterologous polypeptides and, said S-layer is a fusion product of the S-layer protein and the heterologous polypeptide.

This invention provides the means for producing a bioreactor comprising a suitable substrate (e.g. a rotating biological contactor) in which is adhered the above described bacterium. This invention also provides the means for expressing and presenting vaccine candidate epitopes to the environment of the bacterium described above.

DESCRIPTION OF THE DRAWINGS

For better understanding of this invention, reference may be made to the preferred embodiments and examples described below, and the accompanying drawings in which:

Figure 6A:
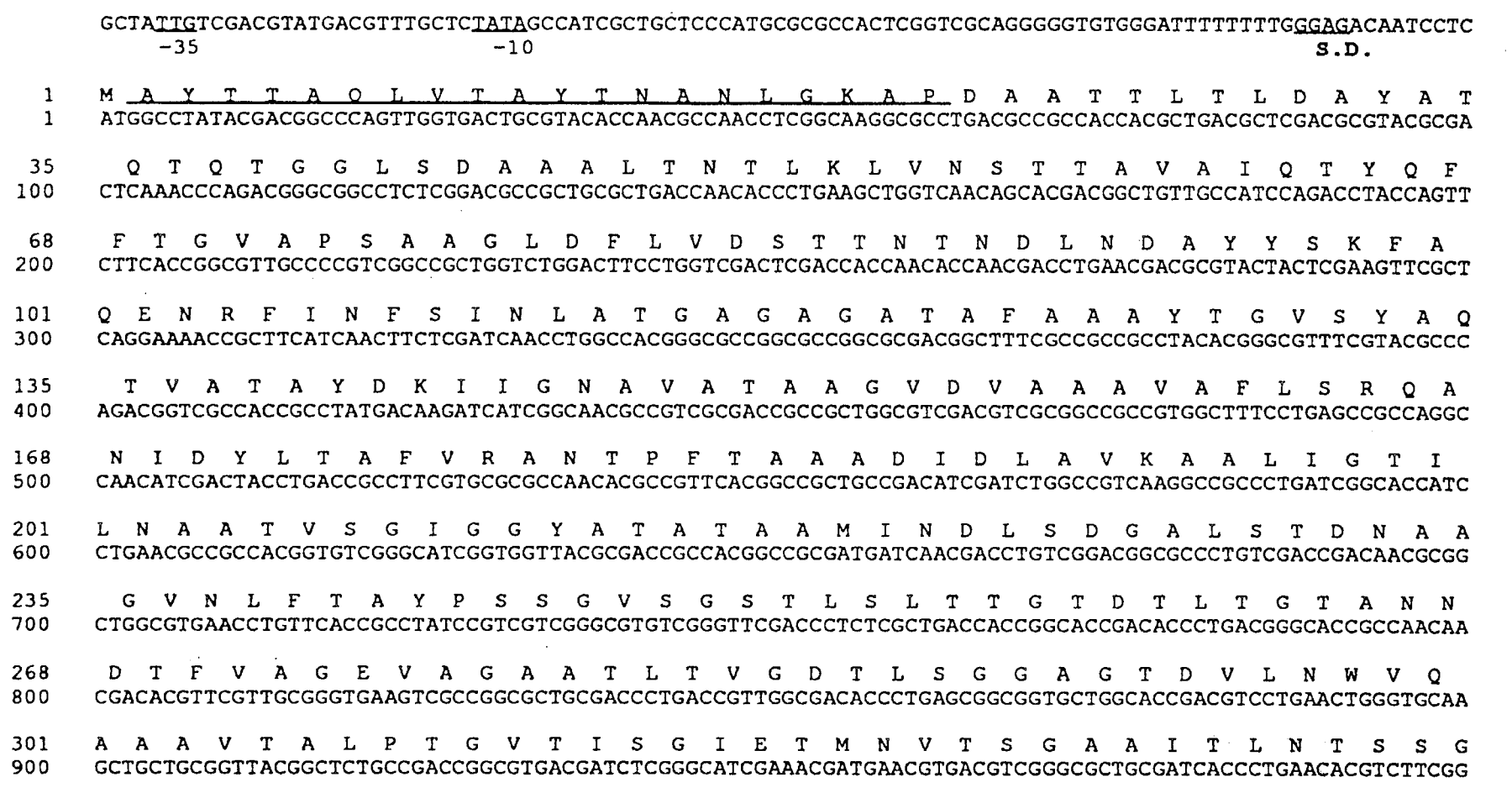
Figure 6B:
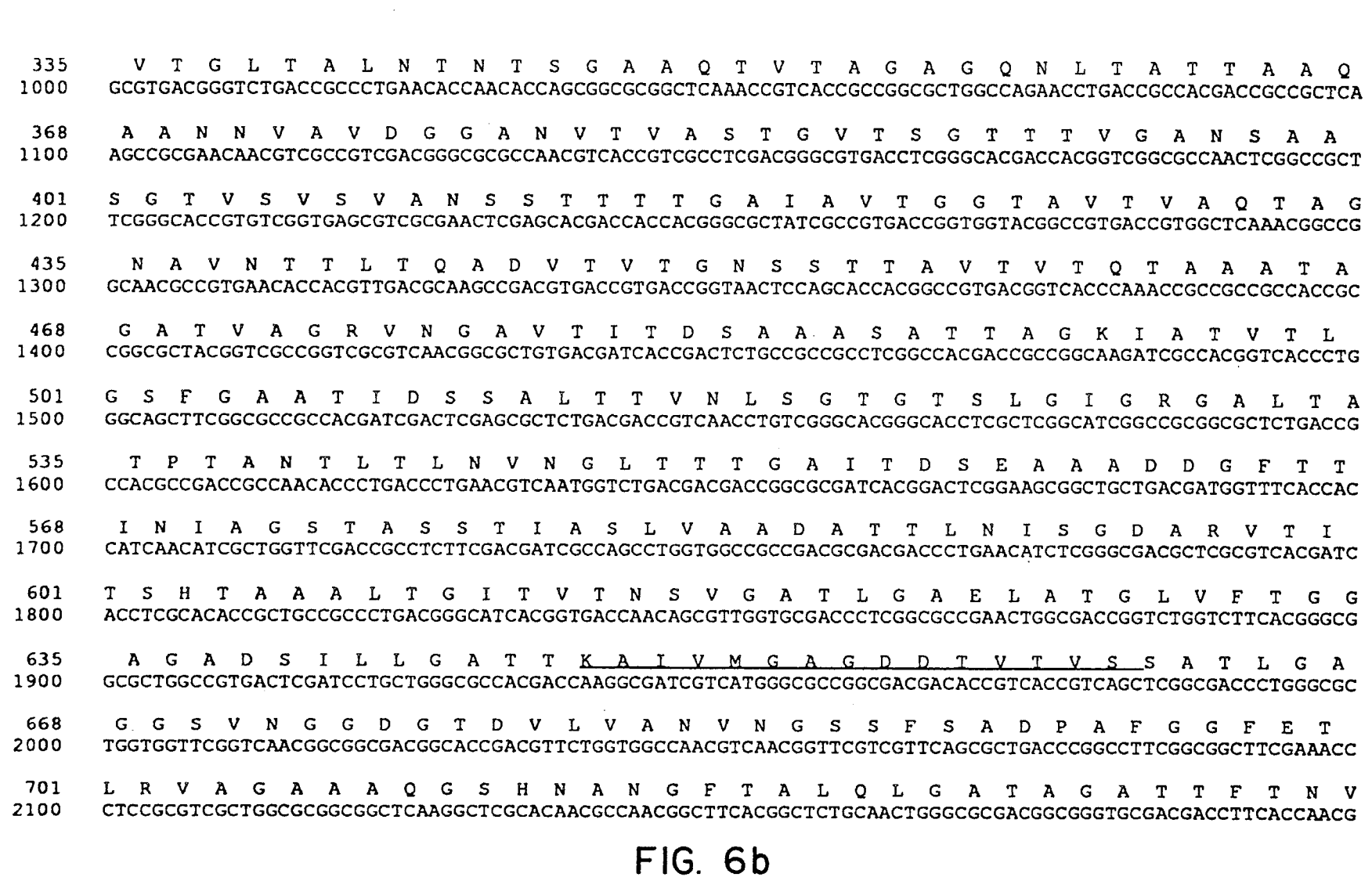

FIG. 6 is the complete nucleotide sequence of the *C. crescentus* rsaA gene (SEQ ID NO:6) and the predicted translational product in the single letter amino acid code (SEQ ID NO:7). The -35 and -10 sites of the promoter region as well as the start of transcription and the Shine-Dalgarno sequence are indicated. Partial amino acid sequences determined by Edman degradation of rsaA protein and of sequenced peptides obtained after cleavage with V8 protease are indicated by contiguous underlining. The putative transcription terminator palindrome is indicated with arrowed lines. The region encoding the glycine-aspartate repeats is indicated by underlined amino acid code letters. This region includes five aspartic acids that may be involved in the binding of calcium ions. The GenBank accession number is M84760.

FIG. 9 is the nucleotide coding sequence (SEQ ID NO:10) and corresponding amino acid sequence (SEQ ID NO:9) in respect of the 110 amino acid IHNV epitope inserted into Caulobacter rsaA gene in Example 6.

DESCRIPTION OF THE PREFERRED EMBODIMENTS

Figure 2:
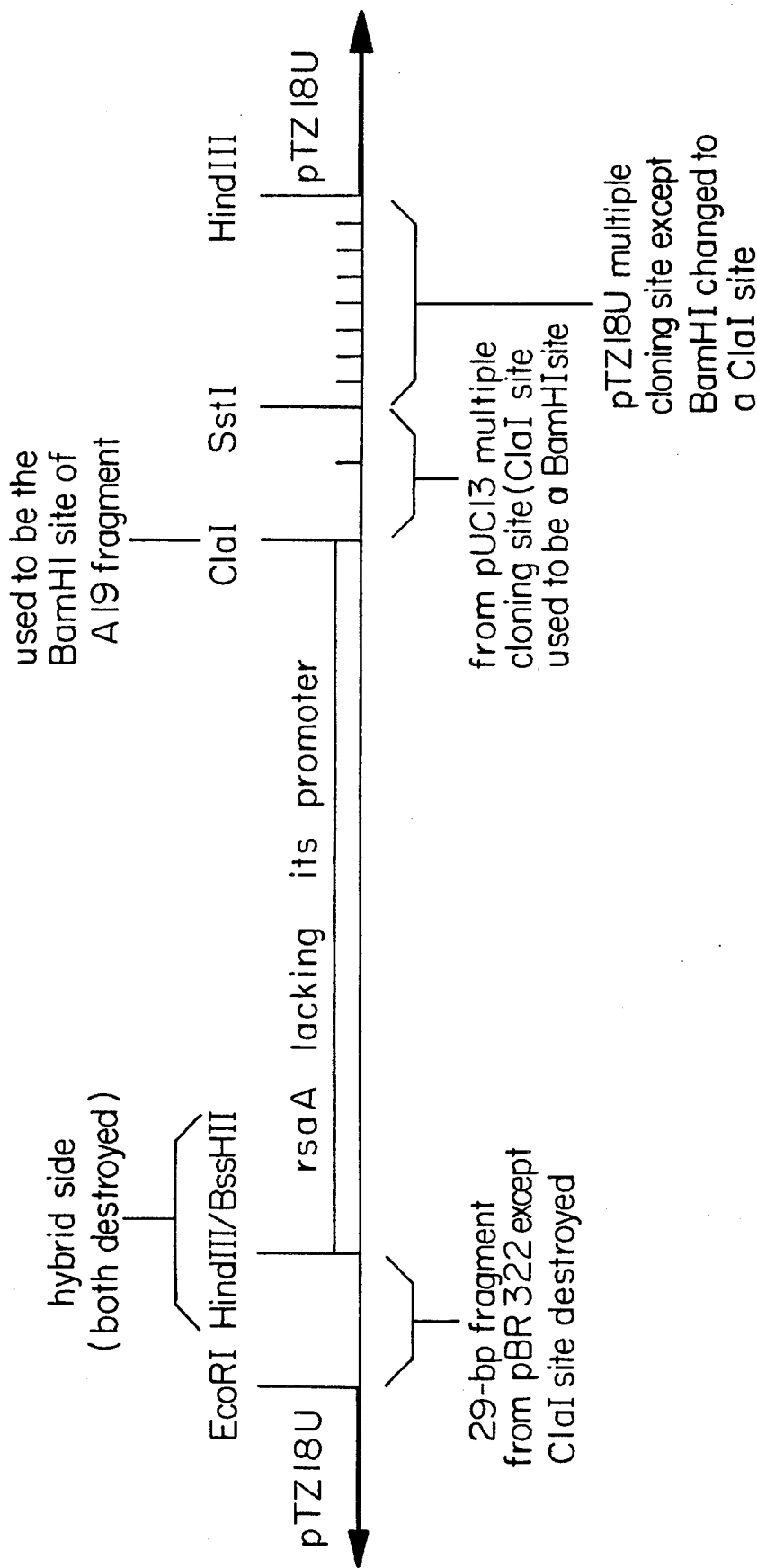
FIG. 2 is a restriction map of a plasmid based promoterless version of the rsaA gene (pTZ18U:rsaAΔP) containing restriction sites and which may be used to accept the heterologous DNA of interest.

A preferred organism for use in this invention is Caulobacter, particularly *C. crescentus*. Most preferred are *C. crescentus* strains such as CB15A containing the rsaA gene encoding the paracrystalline S-layer protein as described in: Gilchrist, A. J. A. Fisher and, J. Smit (1992) "Nucleotide Sequence Analysis Of The Gene Encoding the *Caulobacter crescentus* Paracrystalline Surface Layer Protein". Can. J. Microbiol. 38:193–208.

A heterologous polypeptide referred to herein may be a peptide, polypeptide, protein or a part of a protein. The heterologous polypeptide may be an enzyme, a ligand, an antigen or another functional sequence of amino acids.

Once a particular bacterium's S-layer protein gene is characterized, this invention may be practised by implementing one or more known methods to clone a selected heterologous coding sequence into the S-layer protein gene so that both the S-layer protein and the heterologous sequence are transcribed "in-frame". Knowledge of the S-layer protein gene sequence permits one to identify potential sites to install the heterologous genetic material. The repetitive nature of the S-layer protein results in multiple copies of the heterologous protein being expressed and presented on the surface of the cell.

The following general procedure lays out courses of action and specifies particular plasmid vectors or constructions that may be used to accomplish fusion of an S-Layer protein with a polypeptide of interest. The following description uses the rsaA (S-layer) gene of *C. crescentus* as an example (see FIG. 6 and SEQ ID NO:6). The latter gene sequence is characterized in Gilchrist, A.; J. A. Fisher and, J. Smit (1992) "Nucleotide Sequence Analysis of the Gene Encoding the *Caulobacter crescentus* Paracrystalline Surface Layer Protein". Can. J. Microbiol 38: 193–202, in contrast to an earlier partial characterization now shown to contain some errors (Fisher, J. A.; J. Smit et al, N. Agabian (1988) J. Bacteriol 170:4706–4713).

The general procedure provides detailed steps allowing for the following possibilities:

1) use of an available collection of potentially permissive sites in the S-layer gene to install the genetic information for a polypeptide of interest;

2) use of an available carrier cassette for delivering a gene of interest to sites within the S-layer gene (the cassette offers several advantages over direct modification of a gene of interest, in preparation for insertion);

3) creation of a collection of random insertion sites based on a restriction enzyme of choice, if the available collection of potentially permissive sites is for some reason unsuitable; and, 4) preparation of DNA coding for a polypeptide of interest for direct insertion into permissive sites (ie, not using the carrier cassette) by a method best suited for the particular case (several options are suggested).

The general procedure involves the following steps and alternative courses of action.

As a first step the practitioner will choose an appropriate region (or specific amino acid position) of the S-layer for insertion of a desired polypeptide.

Second, the practitioner will create a unique restriction site in the (preferably hexameric) rsaA (S-layer) gene at position within the gene encoding that region (or corresponding to a specific amino acid) using either standard linker mutagenesis (regional) or site directed mutagenesis (specific amino acid). The unique restriction site is to later act as a site for accepting DNA encoding the polypeptide of interest. The plasmid-based promoter-less version of the rsaA gene (pTZ18U:rsaAΔP) shown in FIG. 2 is preferably used because it contains an appropriate combination of 5' and 3' restriction sites useful for subsequent steps. The restriction site should not occur in rsaA, its carrier plasmid or the DNA sequence coding for the polypeptide of interest.

If it is unclear which region of the S-layer would be suitable for insertion of a polypeptide of interest, a random linker mutagenesis approach is used to randomly insert a unique linker-encoded restriction site (preferably hexameric) at various positions in the rsaA gene. Sites for insertion of the linker are created using an endonuclease, either of a sequence specific nature (eg. tetrameric recognition site restriction enzyme) or sequence non-specific nature (eg. Deoxyribonuclease I [DNase I]). A particularly suitable method is the generalized selectable linker mutagenesis approach based on any desired restriction site of: Bingle, W. H., and J. Smit. (1991) "Linker Mutagenesis Using a Selectable Marker: A Method for Tagging Specific Purpose Linkers With an Antibiotic-Resistance Gene". Biotechniques 10: 150–152. Because endonuclease digestion is carried out under partial digestion conditions, a library of linker insertions at different positions in rsaA is created.

If restriction endonucleases are used to create sites for subsequent insertion of a linker encoding a hexameric restriction site, mutagenesis is preferably done with a mixture of 3 different linkers incorporating appropriate spacer nucleotides in order to satisfy reading frame considerations at a particular restriction site (only 1 of the 3 linker insertions will be useful for subsequent acceptance of DNA encoding the polypeptide of interest). With DNase I, only one linker is needed, but again only 1 of 3 linker insertions may be useful for accepting DNA encoding the polypeptide of interest depending on the position of the DNase I cleavage with respect to the 3 bases of each amino acid codon.

Figure 3:
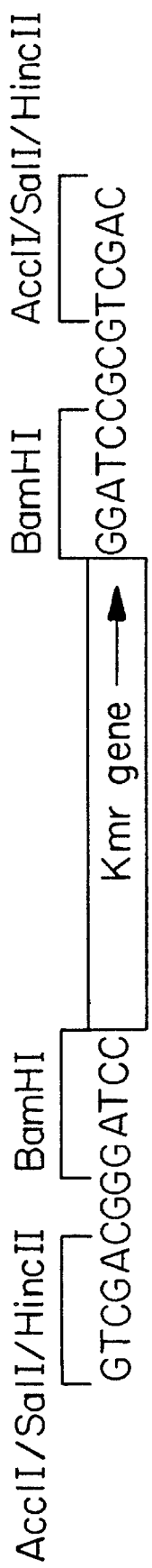
FIG. 3 is the nucleotide sequence of linker BamHI7165K (SEQ ID NO:2; and SEQ ID NO:3) carried in plasmid pUC9B (pUC7165K), which may be used for mutagenesis at sites created in rsaA by a specific or non-specific endonuclease.
Figure 4:
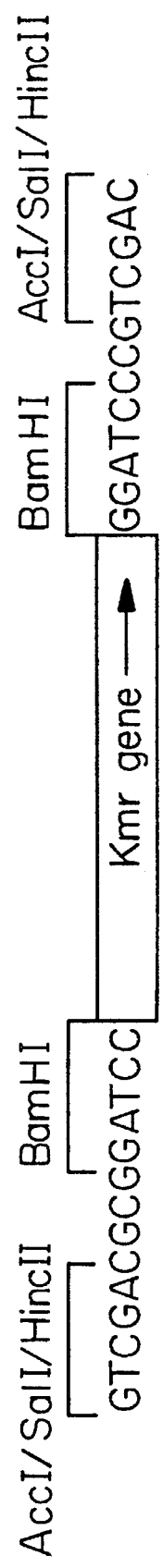
FIG. 4 is the nucleotide sequence a linker BamHI6571K (SEQ ID NO:4; and SEQ ID NO:5) carried in plasmid pTZ19 (pTZ6571K) which may be used for mutagenesis at sites created in rsaA by a specific or non-specific endonuclease.

Next, a linker tagged with a marker is used to insert DNA of interest at a restriction site. For example, if BamHI sites are appropriate as sites for the introduction of DNA encoding a polypeptide of interest, BamHI linkers tagged with a kanamycin-resistance gene for selectable linker mutagenesis may be used. One such 12-bp linker carried in plasmid pUC1021K was described by Bingle and Smit (1991) [supra]. Two additional 15-bp linkers (pUC7165K and pTZ6571K) constructed for creating the other 2 possible translation frames within the linker insert itself are described in FIGS. 3 and 4 (SEQ ID NO:2; SEQ ID NO:3; SEQ ID NO:4; and, SEQ ID NO:5). Any one of the above three kanamycin-resistance tagged BamHI linkers is suitable for mutagenesis at sites created in rsaA by DNase I. As outlined above, a mixture of all three linkers is preferably used for mutagenesis at sites created in rsaA by restriction enzyme digestion.

Once a library composed of linker insertions encoding desired hexameric restriction site at different positions in rsaA has been created, the DNA encoding a polypeptide of interest is inserted into the sites en masse (the library of mutated rsaA genes may be manipulated as one unit). The library is digested with the restriction enzyme specific for the newly-introduced linker encoded restriction site and ligated to a DNA fragment encoding the polypeptide of interest and carrying the appropriate complementary cohesive termini. The DNA specifying the polypeptide of interest can be prepared by a number of standard methods, which may include oligonucleotide synthesis of 2 anti-complementary strands, polymerase chain reaction procedures, or addition of linkers whose termini are compatible with the introduced sites in rsaA to a suitably modified segment of DNA.

Figure 1:
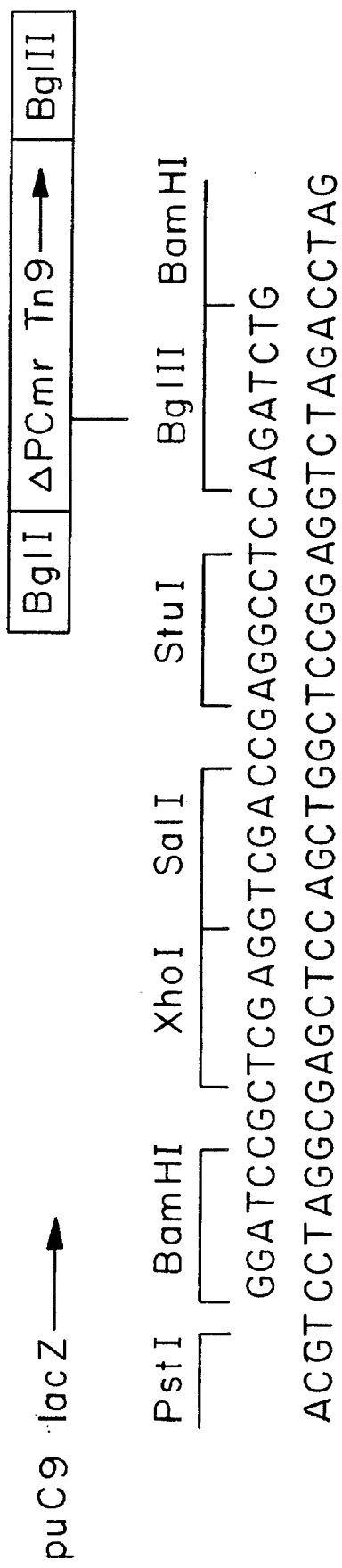
FIG. 1 is the sequence of a carrier cassette which may be cloned into the PstI/BamHI site of pUC9 to deliver a gene sequence of interest to sites within an S-layer protein gene, such as in *Caulobacter crescentus* (SEQ ID NO:1).

In order to facilitate the rapid recovery of useful rsaA genes carrying newly inserted DNA at BamHI sites encoding the polypeptide of interest, the carrier oligonucleotide shown in FIG. 1 may be used. The DNA of interest is first directionally cloned, if possible, using the XhoI, StuI, or SalI sites or non-directionally cloned using any one of the sites in the same orientation as a promoterless chloramphenicol resistance (CmR) gene. To do this the DNA of interest must be provided with the appropriate termini for cloning and spacer nucleotides for maintaining correct reading frame within the cassette and should not contain a BglII site. Pot insertion into the BamHi linker library, the DNA of interest is recovered as a BamHI fragment tagged with a CmR gene. When ligated to the BamHI digested rsaA linker library, only those colonies of the bacterium (eg. E. coli) used for the gene modification steps that are recovered will be those carrying insertions of the desired DNA in the correct orientation, since the promoter on the plasmid is 5' to rsaAΔP and the CmR gene. This eliminates screening for DNA introduction and increases the recovery of useful clones by 100% (1 of 3 versus 1 of 6). While still manipulating the library as one unit, the CmR gene is removed using BglII. The carrier oligonucleotide also provides the opportunity to add DNA 5' or 3' to the DNA of interest at SalI, XhoI or StuI sites providing the DNA of interest does not contain any of these sites. This allows some control over spacing between rsaA sequences and the sequence of the DNA of interest.

Next, the rsaA genes carrying the DNA of interest in the correct orientation is excised from the plasmid (eg. from the pTZ18U:rsaAΔP plasmid) and is transferred to a suitable vector providing a promoter recognized by Caulobacter. Preferably, such a vector is pWB9 or pWB10 (Bingle, W. H., and J. Smit (1990) "High Level Plasmid Expression Vectors for *Caulobacter crescentus* Incorporating the Transcription and Transcription-Translation Initiation Regions of the Paracrystalline Surface Layer Protein Gene". Plasmid 24: 143–148) with EcoRI/SstI sites. Therefore, the DNA of interest should not contain the latter sites. These vectors allow expression of rsaA hybrids in S-layer negative mutants of *C. crescentus* such as CB15KSac (Edwards, P. and, J. Smit (1991) "A Transducing Bacteriophage for *Caulobacter crescentus* Uses The Paracrystalline Surface Layer Protein As a Receptor" J. Bacteriol. 173:5568–5572); or, CB2A described in: Smit, J. and, N. Agabian (1984) J. Bacteriol. 160:1137–1145.

Those Caulobacter surviving transfer are examined for S-layer assembly and presentation of the new polypeptide activity, antigenicity, etc. by methods specific to the needs of the investigator or the capabilities of the inserted sequence. Many of the sites created are "benign" as they have no effect on the functional regions of the protein involved with export, self assembly, etc. However, not every site that results in an absence of functional disruption of the S-layer is best for insertion of new activities. Some sites may not be well exposed on the surface of the organism and other sites may not tolerate insertion of much more DNA than the linker sequence.

Use of the S-layer protein as a vehicle for production and presentation of a heterologous polypeptide has several advantages. Firstly, the S-layer protein is synthesized in large quantities and has a generally repetitive sequence. This permits the development of systems for synthesis of a relatively large amount of heterologous material as a fusion product with an S-layer protein. It may be desirable to retain the fusion product as part of the bacterial cell envelope or, the fusion product may be separated from the organism, such as by the method described in: Walker, S. G.; S. H. Smith; and J. Smit (1992) "Isolation and Comparison of the Paracrystalline Surface Layer Proteins of Freshwater Caulobacters". J. Bacteriol. 174:1783–1792. Alternatively, the Caulobacter strain that is used to express the fusion product may be derived from a strain such as CB15Ca5 that sheds its S-layer (Edwards and J. Smit (1991) [Supra].

Second, this invention is particularly suitable for use in a bioreactor systems. An example would be the use of a modified Caulobacter expressing a polypeptide having the activity of a metallothionein in a bioreactor, to bind toxic metals in sewage, waste water etc. Caulobacters are ideal candidates for fixed-cell bioreactors, the construction of which is well known. An example of such a bioreactor is a rotating biological contactor. Although other bacteria are found in the environment that are capable of binding metals, they often do so by producing copious polysaccharide slimes that quickly plug filtration systems. In some cases, the bacteria are not surface-adherent or the bacteria do not show selectivity towards key toxic metals. By taking advantage of the natural biofilm forming characteristics of Caulobacter, bioreactors may be formed comprising a substrate and a single layer of cells adhered thereon, with the cells distributed at high density. A variety of substrates may be used such as a column of chemically derivatized glass beads or a porous ceramic material such as ceramic foam.

Metallothioneins are small cysteine-rich proteins induced by many organisms in response to exposure to heavy metals. They are generally expressed internally and are designed to limit exposure of other aspects of cell physiology to the toxic metals. Typically, metallothioneins are composed of about 60 amino acids and the genes from a variety of mammalian organisms have been cloned and sequenced. Metallothioneins bind metals such as cadmium, zinc, cobalt, copper and mercury in significant amounts (such as from 4–12 moles of metal per mole of protein). Modification of a Caulobacter such that its S-layer protein is a fusion product with a metallothionein or a polypeptide with a similar activity would provide a useful component for a bioreactor.

Another advantageous application for this invention is in the production of batch cultures of modified Caulobacter wherein the S-layer protein is a fusion product with an enzyme. For example, such Caulobacter could be grown in wood pulp suspensions at an appropriate juncture of the pulping process in order to provide for enzymatic decomposition of the wood-pulp structure (e.g. with an enzyme having an activity like xylanase or cellulase). Such an application may permit more effective penetration of bleaching agents in the wood-pulp bleaching process thereby reducing the use of chlorine-based bleaching agents.

Another advantageous application of this invention is the production of organisms that present vaccine-candidate epitopes at the organism's cell surface. For example, modified Caulobacter may be readily cultured in outdoor freshwater environments and would be particularly useful in fish vaccines. The two-dimensional crystalline array of the S-protein layer of Caulobacter, which has a geometrically regular, repetitive structure, provides an ideal means for dense packing and presentation of a foreign epitope to an immune system.

EXAMPLE 1

Production of Permissive Insertion Sites in C. crescentus

Figure 5:
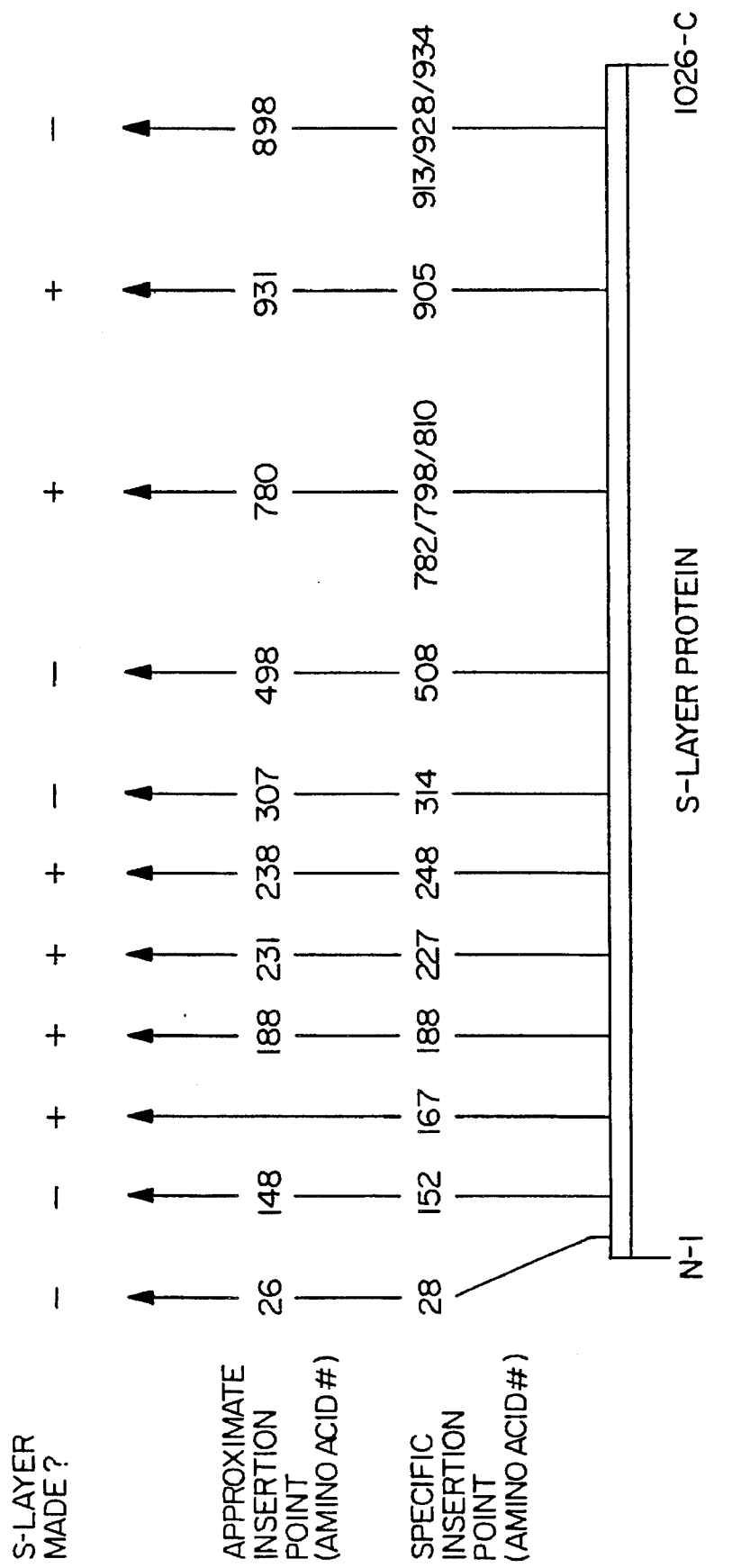
FIG. 5 is a map of 11 insertion events at TaqI sites in the rsaA gene identified by amino acid number of the insertion site in the S-layer protein and scored according to whether the S-layer is produced in the modified organism.

Using the restriction enzyme TaqI, a partial digestion of the rsaA gene in pTZ18U:rsaAΔP produced a group of linearized segments with random TaqI sites cleaved. The linearized segments were modified by use of the tagged linker mutagenesis procedure of Bingle and Smit (1991) [supra], using the 12-bp BamHI linker carried in plasmid pUC102K discussed in the general procedure above. Those products that produced a full-length protein in E. coli were ultimately transferred to pWBI (a minor variation of pWB9 that is replicated by Caulobacter), as described in the general procedure. The resulting construction was introduced into a C. crescentus strain. Distinguishable events were retrieved and analyzed for the ability to produce a full-length protein in C. crescentus and to produce the crystalline S-layer on their surface and the approximate location of the insertion. The results of this screening together with the approximate positions of six successful events (and subsequently determined exact or specific insertion positions) are illustrated in FIG. 5.

The above-described six positive events represent cases where the 4-amino acid insertion is tolerated with no effect on the S-layer function. The S-layers of the modified Caulobacter were indistinguishable from a wild-type S-layer. Thus, they have a higher potential for tolerating the addition of more foreign peptide material than less characterized sites. By producing 3 versions of the gene of interest, representing each possible reading frame (using standard linker addition technology), one may test each of these sites for suitability in expressing the desired activity. Also, by using restriction enzymes other than TaqI (such as AciI, HinPI or MspI) a larger library of BamHI insertions may be created.

EXAMPLE 2

Insertion of Metallothionein Into a Specific Site

An insertion of the above described 12 bp linker was made at the TaqI site that corresponds to amino acid #188, frame #3 (see FIG. 6; SEQ ID NO:6; and, SEQ ID NO:7). This created a unique BamHI site at that position. Because the precise position of the TaqI site could be assessed from the DNA sequence information available for the rsaA gene, the necessary translation frame was known and thus a single construction of the metallothionein gene was made. This was done by excision of the coding sequence of monkey metallothionein II peptide (which is 60 amino acids with a molecular weight of about 5000) at known restriction sites and adapting the gene ends with BamHI linkers with appropriate base pair spacers for the needed translation frame.

After insertion into the BamHI site created at position 188, frame 3, several clones were examined by determining whether they could bind elevated levels of cadmium. This is a functional assay for the metallothionein, explained in more detail below. The assay was necessary because the segment had equal probability of being inserted backwards. One clone that gave positive results was examined by electron microscopy and the presence of a normal S-layer was confirmed. The plasmid in the clone that gave positive results was also examined by DNA sequencing analysis, sequencing across the junction between the position 188 site and the 5' side of the metallothionein gene. The sequence data confirmed correct orientation.

The plasmid-containing clone and relevant control strains were examined for the ability to bind several metals known to be bound by native metallothionein. This was done by growing the strains of bacteria in the presence of the metals at a concentration of 5 µg/ml. After extensive washing of the cells to remove unbound metal, the cells were ashed by treatment at 500° C. and the residue was dissolved in dilute nitric acid and examined for metal content by atomic absorption spectroscopy. The results from one round of data collection is shown in Table 1. In the case of cadmium and copper, an elevated level of bound metal is noted in the metallothionein-expressing strains.

TABLE 1

| Caulobacter | Metal Ion Tested (µg/metal/ OD unit of cells) | | | |
| --- | --- | --- | --- | --- |
| | Copper Trial | | Cadmium | Zinc |
| | 1 | 2 | | |
| CB15 (wild-type,S-layer[+]) | 1.79 | 1.0 | 0.71 | 4.15 |
| CB15KSAC (S-layer negative strain) | 2.18 | 1.33 | 1.07 | 4.08 |
| CB15KSAC/p188.3 (containes S-layer with linker insert only) | 2.01 | 1.30 | 11.1 | 3.66 |
| CB15KSAC/p188.3MT (S-layer with Metallothionein inserted) | 2.79 | 3.09 | 19.1 | 3.00 |

EXAMPLE 3

Investigation of Other Permissive Sites in rsaA Gene

A library of 240 BamHI linker insertions was created using the procedures of Example 1. Of the 240 insertions, 45 target sites in the rsaA gene were made with TaqI. 34 of the latter insertions were discarded because the clones contained deletions of rsaA DNA as well as the linker insertions. The remaining 11 resulted in 5 non-permissive and the 6 permissive sites described in Example 1. The remaining 195 insertions in the library were made using the enzymes HinPI, AciI, and MspI to create target sites as outlined in Example 1. Of the latter 195 insertions, 49 permissive sites were located for a total of 55. Of those sites scored as non-permissive, some may have had deletions of rsaA DNA at the linker insertion site.

Figure 7:
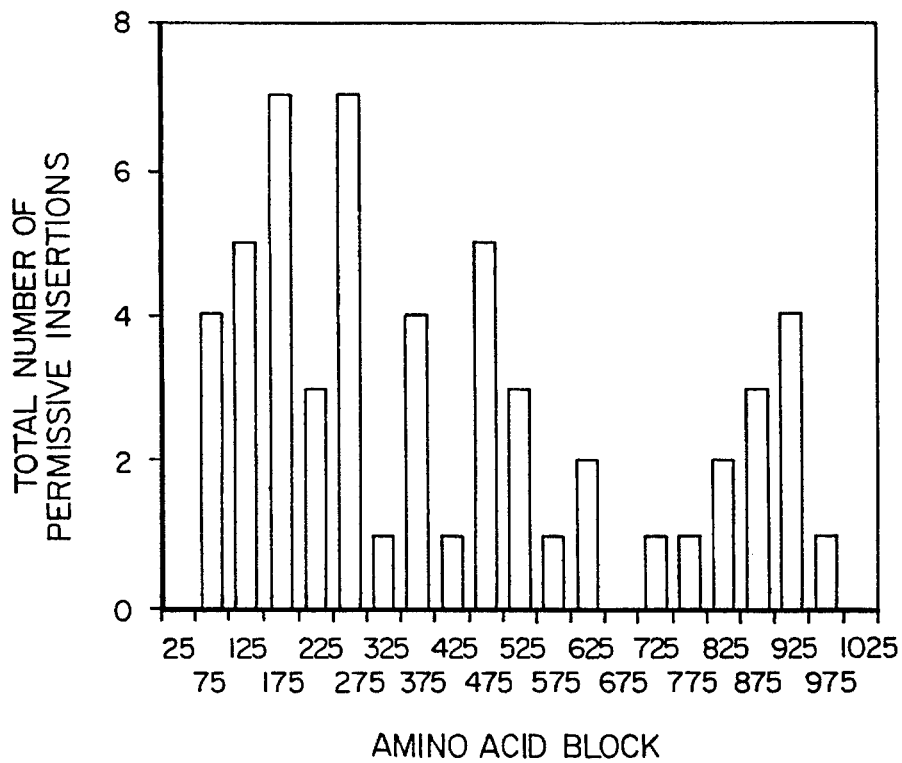
FIG. 7 is a bar graph showing the approximate location by amino acid block of 55 permissive sites in the rsaA gene corresponding to TaqI, HinPI, AciI, and MspI sites described in Example 3.

The results of the screening for permissive sites using the above-mentioned restriction enzymes is shown in FIG. 7 which illustrates the approximate location of the 55 permissive sites. While most of the TaqI sites may be specifically identified from the rsaA gene sequence, many of the sites for the other restriction enzymes are only known by their approximate location in the gene since closely spaced alternate sites are known from the rsaA sequence. The results show that sites that will accept 2–4 amino acids while still allowing the protein to be made and assembled into an S-layer are scattered up and down the protein. Furthermore, there is an unexpectedly high proportion of sites at which such insertions do not prevent expression and assembly of the S-layer. The results indicate that approximately 25–50% of in-frame linker insertions will be tolerated by the S-layer protein and the Caulobacter and that diverse regions of the protein will tolerate insertions. Thus, Caulobacter is an ideal candidate for expression of polypeptides fused with the S-layer and the presence of multiple permissive sites extending along the rsaA gene will permit the insertion of a plurality of the same or different peptides into the same rsaA protein molecule and expressed on the surface of a single Caulobacter.

EXAMPLE 4

Further Studies with Metallothionein

The results described for Example 3 indicate that it may be possible to insert metallothionein at multiple places in the rsaA protein and thereby enhance the metal binding capacity of such a transformed Caulobacter. However, when the procedures of Example 2 were repeated to insert the metallothionein coding sequence into the 55 permissive sites identified in the preceding Example, the transformed Caulobacter did not synthesize an S-layer. Furthermore, the transformed Caulobacter of Example 2 is stable as long as the transformants are frozen immediately after isolation. When continuously cultured for approximately one week, the tranformants delete the metallothionein portion of the S-layer and the S-layer protein returns to its normal size. Consideration of the predicted amino acid sequence of the rsaA protein shows that the latter protein lacks cysteine residues whereas metallothionein has a high cysteine content. It appears that for long term expression of a fusion product with rsaA protein, the heterologous polypeptide should not have a high cysteine content and preferably, not be capable of producing an internal disulphide bond in an aerobic environment.

EXAMPLE 5

Expression and Presentation of Antigenic Epitomes on Caulobacter Cell Surface

Figure 8:
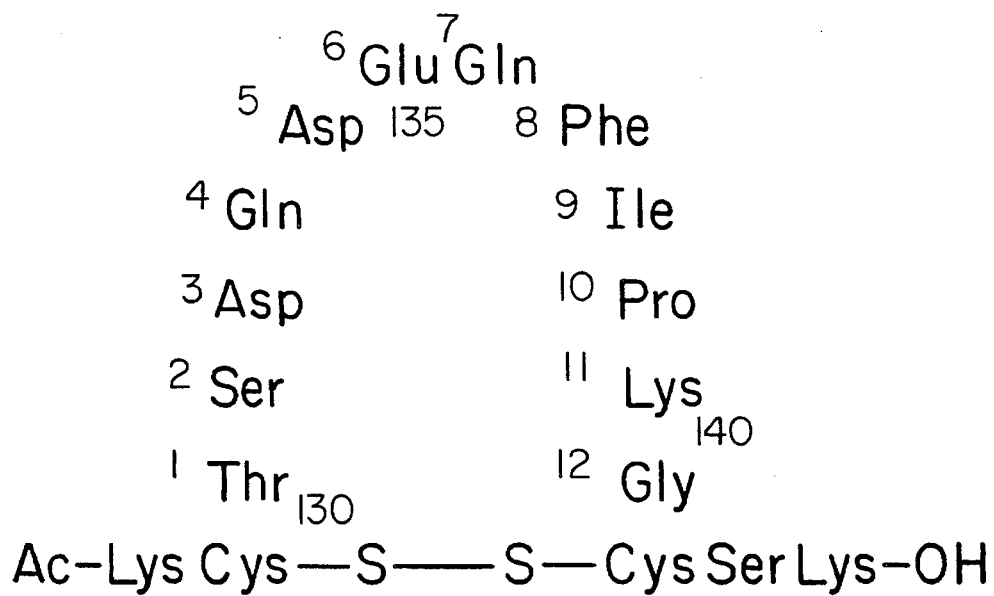
FIG. 8 is a portion of an amino acid sequence (SEQ ID NO: 8) from *P. aeruginosa* PAK pilin in which the 12 amino acid epitope employed in Example 5 is identified by superscript numerals 1–12.

Using the library of the 49 permissive sites other than those made with TaqI described in Example 3, the coding sequence for a 12-amino acid epitope lacking cysteine residues from *Pseudomonas aeruginosa* PAK pilin was inserted at the sites using the procedures described above and employing the carrier cassette shown in FIG. 1. DNA coding for the pilus epitope shown in FIG. 8 (SEQ ID NO:8) consisting of the amino acids numbered 1–12 in superscript was prepared by oligonucleotide synthesis of two anti-complementary strands. The transformed bacteria were screened for both production and presentation of the epitopes by the transformed Caulobacter by using standard Western immunoblot analysis (see: Burnette, W. N. 1981 "Western Blotting; Electrophoretic Transfer of Protein from Sodium Dodecyl-Polyacrylamide Gels to Unmodified Nitrocellulose and Radiographic Detection Antibody and Radioiodinated Protein A"; Analytical Biochemistry 112:195–203) and by colony immunoblot tests in which the cells were not disrupted (see: Engleberg, N. C., et al 1984 "Cloning an Expression of *Legionella pneumophilia* Antigens in *Escherichia coli*"; Infection and Immunity 44:222–227). Anti-pilus monoclonal antibody obtained from Dr. William Paranchych, Dept. of Microbiology, University of Alberta (Canada) was used in the immunoblot analyses to detect the presence of the pilus epitope insert. The antibody (called PK99H) was prepared using purified *Pseudomonas aeruginosa* PAK pilin as the antigen and the monoclonal antibody against the 12 amino acid epitope was isolated by standard techniques using BALB/C mice as a source of ascites fluid. Reaction with the antibody in the whole cell colony immunoblot assay shows that the epitope is not only expressed in the transformed Caulobacter but is exposed on the S-layer surface overlying the cell in such a way that the epitope is available to the antibody. Of the organisms screened, insertions of the pilus epitope at the following sites in the rsaA gene (identified by restriction enzyme and approximate amino acid position) resulted in a positive reaction with the antibody in the whole cell Colony immunoblot analysis: HinPI 288, 538, and 671; AciI at 438; and, MspI at 95, 521, 638, 705, 588, and 905. The results show that the permissive sites that will accept polypeptides of the size of the pilus epitope are numerous and scattered across the rsaA gene. Furthermore, analysis of the transformants indicated that multiple copies of the pilus epitope were successfully inserted at the sites made with MspI at approximate amino acid position 638.

EXAMPLE 6

Insertion of Large Polypeptides

Bacterial surface proteins from organisms other than Caulobacter described in the prior art are not known to accept polypeptides larger than about 60 amino acids within the structure of the surface protein. The procedures of the preceding Example were carried out in order to insert the coding sequence of a 110 amino acid epitope from IHNV virus coat glycoprotein at the approximate insertion sites identified in the preceding Examples as 521; 588; 638; and 705. The IHNV epitope coding sequence was prepared by PCR and had the sequence shown in FIG. 9 (SEQ ID NO:10) which corresponds to amino acid residues 335–444 of the IHNV sequence described in: Koener, J. F. et al 1987 "Nucleotide Sequence of a cDNA Clone Carrying the Glycoprotein Gene of Infectious Hematopoietic Necrosis Virus, a Fish Rhabdovirus"; Journal of Virology 61:1342–1349. Anti-IHNV polyclonal antibody against whole IHNV obtained from Dr. Joann Leong, Dept. of Microbiology, Oregon State University, U.S.A. (see: Xu, L. et al 1991 "Epitope Mapping and Characterization of the Infectious Hematopoietic Necrosis Virus Glycoprotein, Using Fusion Proteins Synthesized in *Escherichia coli*"; Journal of Virology 65:1611–1615) was used in the immunoblot assays described in the preceding Example to screen for Caulobacter that express and present the IHNV sequence on the surface of the S-layer of the Caulobacter. Reaction in the whole cell colony immunoblot assay was positive in respect of insertions at approximate site locations 521 and 705, and negative at approximate site locations 588 and 638. The IHNV insert contains a single cysteine residue and is an extremely large insert for successful expression as a fusion product with a bacterial surface protein. Yet, 50% of the sites tested resulted in successful production and presentation of the epitope on the cell surface.

This invention now being described, it will be apparent to one of ordinary skill in the art that changes and modifications can be made thereto without departing from the spirit or scope of the appended claims.

We claim:

1. A method of expressing and presenting to the environment of a Caulobacter a polypeptide that is heterologous to an S-layer protein of the Caulobacter, which method comprises cloning a coding sequence for a heterologous polypeptide in-frame into a rsaA gene of the Caulobacter whereby the polypeptide is expressed and presented to the environment of the Caulobacter as a fusion product with S-layer protein of the Caulobacter, wherein the heterologous polypeptide lacks the capacity of participating in the formation of a disulphide bond within said fusion product when expressed by the Caulobacter.

2. The method of claim 1, wherein the heterologous polypeptide is cloned into the rsaA gene at: a TaqI site at amino acid position 188; HinPI sites at approximately the amino acids positions 288, 538 and 671; a AciI site at approximately the amino acid position 438; or, MspI sites at approximately the amino acids positions 95, 521, 638, 705, 588 and 905.

3. The method of claim 2, wherein the heterologous polypeptide is cloned into MspI sites at approximately the amino acid positions 521 and 705.

4. The method of claim 1, comprising the additional step of culturing the Caulobacter.

5. The method of claim 4, wherein the Caulobacter is cultured as a film in a bioreactor.

\* \* \* \* \*

UNITED STATES PATENT AND TRADEMARK OFFICE
CERTIFICATE OF CORRECTION

PATENT NO. : 5,500,353

DATED : March 19, 1996

INVENTOR(S) : John Smit and Wade H. Bingle

It is certified that error appears in the above-identified patent and that said Letters Patent is hereby corrected as shown below:

Fig. 6a, replace nucleotide position number "1" with --101--.

Fig. 6a, replace nucleotide position number "100" with --201--.

Fig. 6a, replace nucleotide position number "200" with --301--.

Fig. 6a, replace nucleotide position number "300" with --401--.

Fig. 6a, replace nucleotide position number "400" with --501--.

Fig. 6a, replace nucleotide position number "500" with --601--.

Fig. 6a, replace nucleotide position number "600" with --701--.

Fig. 6a, replace nucleotide position number "700" with --801--.

Fig. 6a, replace nucleotide position number "800" with --901--.

Fig. 6a, replace nucleotide position number "900" with --1001--.

Fig. 6b, replace nucleotide position number "1000" with --1101--.

UNITED STATES PATENT AND TRADEMARK OFFICE
CERTIFICATE OF CORRECTION

PATENT NO.  : 5,500,353

DATED       : March 19, 1996

INVENTOR(S) : John Smit and Wade H. Bingle

It is certified that error appears in the above-identified patent and that said Letters Patent is hereby corrected as shown below:

Fig. 6b, replace nucleotide position number "1100" with --1201--.

Fig. 6b, replace nucleotide position number "1200" with --1301--.

Fig. 6b, replace nucleotide position number "1300" with --1401--.

Fig. 6b, replace nucleotide position number "1400" with --1501--.

Fig. 6b, replace nucleotide position number "1500" with --1601--.

Fig. 6b, replace nucleotide position number "1600" with --1701--.

Fig. 6b, replace nucleotide position number "1700" with --1801--.

Fig. 6b, replace nucleotide position number "1800" with --1901--.

Fig. 6b, replace nucleotide position number "1900" with --2001--.

Fig. 6b, replace nucleotide position number "2000" with --2101--.

Fig. 6b, replace nucleotide position number "2100" with --2201--.

UNITED STATES PATENT AND TRADEMARK OFFICE
CERTIFICATE OF CORRECTION

PATENT NO.  : 5,500,353

DATED       : March 19, 1996

INVENTOR(S) : John Smit and Wade H. Bingle

It is certified that error appears in the above-identified patent and that said Letters Patent is hereby corrected as shown below:

Fig. 6c, replace nucleotide position number "2200" with --2301--.

Fig. 6c, replace nucleotide position number "2300" with --2401--.

Fig. 6c, replace nucleotide position number "2400" with --2501--.

Fig. 6c, replace nucleotide position number "2500" with --2601--.

Fig. 6c, replace nucleotide position number "2600" with --2701--.

Fig. 6c, replace nucleotide position number "2700" with --2801--.

Fig. 6c, replace nucleotide position number "2800" with --2901--.

Fig. 6c, replace nucleotide position number "2900" with --3001--.

Fig. 6c, replace nucleotide position number "3000" with --3101--.

Fig. 6c, replace nucleotide position number "3100" with --3201--.

Fig. 6b, amino acid residue 377, replace "G" with --R--.

UNITED STATES PATENT AND TRADEMARK OFFICE
CERTIFICATE OF CORRECTION

PATENT NO.   : 5,500,353

DATED        : March 19, 1996

INVENTOR(S)  : John Smit and Wade H. Bingle

It is certified that error appears in the above-identified patent and that said Letters Patent is hereby corrected as shown below:

Fig. 6b, amino acid residue 637, replace "A" with --R--.

Fig. 6c, amino acid residue 843, replace "G" with --A--.

Fig. 6c, amino acid residue 844, replace "S" with --P--.

Fig. 9, change the codon of cys 23 from "TCC" to --TGC--.

Col. 17, amino acid residue 377, replace "G" with --R--.

Col. 20, amino acid residue 637, replace "A" with --R--.

Col. 22, amino acid residue 843, replace "G" with --A--.

Col. 22, amino acid residue 844, replace "S" with --P--.

Col. 23, SED ID NO:10, nucleotide 68, replace "C" with --G--.

Signed and Sealed this

Seventeenth Day of November, 1998

*Attest:*

BRUCE LEHMAN

*Attesting Officer*    *Commissioner of Patents and Trademarks*